United States Patent [19]

Arrhenuis

[11] Patent Number: 5,403,928
[45] Date of Patent: Apr. 4, 1995

[54] FLUORESCENT MARKER COMPONENTS AND FLUORESCENT PROBES

[75] Inventor: Peter O. G. Arrhenuis, San Diego, Calif.

[73] Assignee: Diatron Corporation, San Diego, Calif.

[21] Appl. No.: 701,449

[22] Filed: May 15, 1991

Related U.S. Application Data

[63] Continuation of Ser. No. 523,601, May 15, 1990, abandoned.

[51] Int. Cl.$^6$ ............ C09B 47/30; C07D 487/22
[52] U.S. Cl. .................. 540/128; 540/472; 540/121
[58] Field of Search ............... 540/121, 128, 140, 145, 540/465, 474, 472; 524/88, 90; 536/17.1; 436/536; 530/324

[56] References Cited

U.S. PATENT DOCUMENTS

| | | | |
|---|---|---|---|
| 2,951,797 | 9/1960 | Sharp | 540/121 |
| 3,116,256 | 12/1963 | D'Alelio et al. | 524/88 |
| 3,287,470 | 11/1966 | Pugin et al. | 106/410 |
| 4,104,466 | 8/1978 | Tsuchida et al. | 540/145 |
| 4,614,723 | 9/1986 | Schmidt et al. | 436/536 |
| 4,707,454 | 11/1987 | Hendrix | 436/546 |
| 4,732,570 | 3/1988 | Baumgartner et al. | 524/88 |
| 4,822,733 | 4/1989 | Morrison | 435/6 |
| 4,822,877 | 4/1989 | Inada et al. | 540/145 |
| 4,849,207 | 7/1989 | Sakata et al. | 424/1.1 |
| 4,877,872 | 10/1989 | Morgan et al. | 540/145 |
| 5,053,423 | 10/1991 | Liu | 514/410 |
| 5,059,510 | 10/1991 | Jones et al. | 540/121 |
| 5,135,717 | 8/1992 | Renzoni et al. | 540/128 |
| 5,177,200 | 1/1993 | Kluger et al. | 524/88 |

FOREIGN PATENT DOCUMENTS

| | | | |
|---|---|---|---|
| 0260098 | 9/1987 | European Pat. Off. | 424/9 |
| 215689 | 9/1988 | Japan | 536/17.4 |
| 3264674 | 11/1988 | Japan | 524/88 |

OTHER PUBLICATIONS

Grant and Hackh's Chemical Dictionary, New York, New York, McGraw Hill Books (1981), p. 241.
Leznoff et al., Phthalocyanines, vol. 2, Weinheim VCH (1993), pp. 30–31 and 168–170.
Gunter Meyer et al, Die Angewandte Makromolekulare Cheme, 72:173 (1978).
Monica Hartman et al, Die Makromolekulare Cheme, 176:831 (1975).
Hartman et al., Chemical Abstracts, vol. 83 (1975), Abstract 79670p.
Meyer et al., Chemical Abstracts, vol. 90 (1979), Abstract 104387f.
Toshio Machiko & David Dolphin, Porphyrins, Hydroporphyrins, Azaporphyrins. Phthalocyanines, Corroles, Corrins and Related Macrocycles 21.1 813–898, 1978.
Moser, et al. The Phthalocyanines, vol. 1, [CRC Press, Boca Raton Fla., 1990], pp. 123–127.
Merck Index (Rahway, N.J., Merck & Co., 1989) p. 172.

Primary Examiner—Mukund J. Shah
Assistant Examiner—P. K. Sripada
Attorney, Agent, or Firm—Lyon & Lyon

[57] ABSTRACT

Marker components are provided which are compatible with aqueous solutions, exhibit favorable fluorescence properties and exhibit decreased non-specific binding to macromolecules in solution. These marker components are useful in applications such as fluorescence immunoassays, in vivo imaging and in vivo tumor therapy.

22 Claims, 1 Drawing Sheet

| COMPOUND | R$_1$ | R$_2$ = R$_3$ |
|---|---|---|
| II | ImSi | H |
| III | PEG-Si | H |
| V | Cl | CN |
| VI | OH | COOH |
| VII | ImSi | COOH |
| VIII | PEG-Si | COOH |

| COMPOUND | R₁ | R₂ = R₃ |
|---|---|---|
| II | ImSi | H |
| III | PEG - Si | H |
| V | Cl | CN |
| VI | OH | COOH |
| VII | ImSi | COOH |
| VIII | PEG - Si | COOH |

FLUORESCENT MARKER COMPONENTS AND FLUORESCENT PROBES

FIELD OF THE INVENTION

This application is a continuation of 07/523,601, filed May 15, 1990, which is now abandoned.

The present invention is directed to marker components useful as fluorescent labels useful in immunoassays, to fluorescent probes and to methods of preparing such marker components and probes.

BACKGROUND OF THE INVENTION

Publications and other reference materials referred to herein are incorporated herein by reference and are numerically referenced in the following text and respectively grouped in the appended Bibliography which immediately precedes the claims.

The detection of small quantities of a substance in solution can be accomplished by fluorescence labeling. For example, the detection of analytes in human serum has been achieved by time-resolved fluoroimmunoassay or fluorescence polarization immunoassay (Ref. 1 to 3).

Dyes which have been used extensively as fluorescent labels in probes and immunoassays include fluorescein derivatives such as fluorescein isothiocyanate, rhodamine derivatives and derivatives of the chelates of rare earth metals such as europium. (Ref. 5, 7)

Certain physical and chemical properties of a dye may contribute to determining its overall utility as a fluorescent label, e.g. for homogeneous fluoroimmunoassay and/or probe in the detection of analyte. Important properties include fluorescence intensity, fluorescence lifetime, excitation and emission wavelength maxima, polarization and non-specific binding behavior.

(a) Fluorescence Intensity: The intensity of the fluorescence produced upon excitation of the probe with light (such as from a laser source). The nature of the solvent used for the fluorescence measurement may have a significant effect on the intensity of the fluorescence of a given probe. Use of aqueous solvent systems, such as biological buffers is convenient and possibly essential in applications such as immunoassays. Self-aggregation of the probes in these solvents may substantially attenuate their fluorescence intensity.

(b) Excitation and Emission Wavelengths: The wavelength of light required to efficiently produce fluorescence and the wavelength of light at which fluorescence emission occurs. (Fluorescence emission occurs at a longer wavelength than the excitation wavelength.) Ultraviolet, visible and infrared light (typically wavelengths in the range of about 200 nanometers to about 1000 nanometers) are considered to be wavelengths which are potentially useful in exciting a dye molecule and thereby producing detectable fluorescence. Due to the abundance of naturally occurring substances which fluoresce upon excitation at relatively short wavelengths (in the range of about 200 nm to about 500 nm), improved sensitivity of detection may be achieved by using a probe having a fluorophore which fluoresces upon excitation by light of wavelength greater than about 500 nm, preferably in the spectral range of about 500 nm to about 900 nm. (Ref. 5)

(c) Fluorescence Lifetime and Fluorescence Decay Time: The lifetime of the fluorescence produced by the probe may vary, from less than one nanosecond to several milliseconds. Most organic dyes which exhibit fluorescence lifetimes in the range of 3 to 50 nanoseconds belong to the general class of compounds commonly referred to as aromatic compounds and are exemplified by aromatic hydrocarbon derivatives such as perlene carboxylic acid and aromatic heterocyclic compounds such as phthalocyanines and naturally occurring porphyrins. These dyes have a characteristic fluorescence lifetime, that is, the time period following excitation during which they emit light and during which the fluorescence intensity decreases to about 37% (1/e) of its initial value in the absence of any deactivating factors. The measured fluorescence decay time is the time period during which the decrease to the 37% (1/e) level of fluorescence intensity is observed in realistic situations. The measured decay time of a particular compound may be solvent dependent. Under conditions which minimize deactivation, measured decay time may approach fluorescence lifetime. In order to be suitable for use in an assay such as a fluorescence polarization immunoassay, the measured fluorescence decay time (and necessarily fluorescence lifetime also) of the probe must be suitably long (at least about 2 nanoseconds, preferably on the order of about 20 nanoseconds). Additionally, probes having extended fluorescence decay times allow for improved detection of signal relative to the natural fluorescence background of a sample containing serum.

(d) Fluorescence Polarization: When a fluorescent substance in solution is excited with polarized light, it emits partially polarized light as fluorescence. The degree of polarization of fluorescence can be measured, and is related to the molecular volume of the fluorophore. This relationship can be used to determine the extent of binding of small fluorescent probes serving as haptens to relatively large antibodies.

(e) Non-Specific Binding: The ability of the probe to remain unbound in solution in the presence of large protein molecules such as human serum albumin (MW about 70,000). Nonspecific binding of the small (low molecular weight) dye molecules to relatively large (high molecular weight) macromolecules such as proteins in solution has been observed. (Ref. 14) The occurrence of this noncovalent association between a fluorescent probe and a biological macromolecule is manifested in the fluorescence behavior of the probe-macromolecule complex. Generally, fluorescence polarization is affected. In applications such as homogenous fluorescence immunoassays, it is essential that non-specific binding of the probe to biological macromolecules is kept to a minimum, if not eliminated.

Non-specific binding in immunoassays has always been a troublesome problem, especially if serum samples are involved. In order to circumvent the difficulties caused by non-specific binding, investigators in the past have resorted to the addition of various surfactants such as sodium dodecyl sulfate and chaotropic ions such as potassium trichloracetate or to the precipitation of the serum proteins with protein precipitants such as sulfosalicylic acid followed by a separation step such as centrifugation or filtration to remove the precipitate.

While a separation step solves the problem of nonspecific binding it makes the assay time-consuming, expensive and difficult to automate. Also, the various additives mentioned invariably interfere not only in the non-specific binding but to varying extents in the specific binding by antibody as well. this effect is fully to be expected since the types of interactions in specific and non-specific binding are the same, viz., electrostatic, hydrogen bonding and hydrophobic interactions. Hence, these methods have not proven satisfactory, some differential effect being the best that can be expected.

Most of the non-specific binding of serum is due to the presence of serum albumin. This protein has several specialized functions among which is the carriage of a variety of organic metabolites such as fatty acids and steroid hormones and in addition it carries other substances ingested orally or received by injection. The structure of serum albumin is somehow uniquely suited to this function and when tested in vitro can be shown to bind nearly every type of molecule up to a molecular weight range of a few thousand.

Organic dyes, especially those with aromatic and/or polycyclic structures, may have limited solubility in aqueous solutions and may aggregate in aqueous solvents. (Ref. 4) Fluorescent dyes which are hydrophobic can be modified in order to promote solubility in water; for example, by sulfonation of the dye or dye precursors. (Ref. 6) In general, where an organic molecule has limited solubility in water, improved solubility can be achieved by chemically bonding the organic molecule to one or more water solubilizing groups. Additional examples of such groups are phosphate, carboxylate and quaternary ammonium, and their salts such as sodium and potassium phosphates and ammonium halides.

Porphyrin and phthalocyanine derivatives are useful as fluorophores and exhibit good fluorescent behavior in organic solvents. However, underivatized porphyrin and phthalocyanine compounds are essentially water insoluble and, thus, are highly aggregated in aqueous solutions and exhibit low fluorescence intensity. Modification of porphyrin and phthalocyanine compounds by attaching solubilizing groups such as sulfonate, quaternary ammonium, carboxylate and the like, has improved the water solubility of these compounds; however, the derivatized porphyrins and phthalocyanines often exhibit substantially decreased fluorescence intensity in aqueous solution as opposed to in organic solvents. In addition the water-soluble derivatives have been found to bind tightly in a non-specific manner to components of human serum which limits their usefulness in immunoassays.

Phthalocyanine and porphyrin derivatives have found application in the area of tumor therapy (Ref. 8,9). Water soluble derivatives of these compounds have been prepared. For example, the metallated and sulfonated phthalocyanine, hydroxyaluminum phthalocyanine tetrasulfonic acid, is essentially monomeric in aqueous solutions and efficiently produces fluorescence in water. (Ref. 10, 16). Without exception, however, these previously described fluorophores retain a strong tendency to bind nonspecifically to solution components such as human serum albumin.

SUMMARY OF THE INVENTION

The present invention is directed to detectably labelled marker components which comprise a fluorophore moiety which is linked to a solubilizing polyoxyhydrocarbyl moiety and to methods for preparing these marker components. The present invention is also directed to detectably labelled probes which use these marker components as fluorescent or phosphorescent labels.

The marker components of the present invention are particularly suitable as detectable labels for use in assays for detecting an analyte in aqueous solution. These marker components are useful as fluorescent labels for incorporation in fluorescent probes. Some of these marker components are useful as phosphorescent labels. These components are also useful as labels for agents for in vivo imaging and also as labels for agents used for in vivo tumor therapy.

According to the present invention, marker components are provided which comprise a fluorophore moiety linked to a at least one solubilizing polyoxyhydrocarbyl moiety. Preferably these marker components comprise from about 1 to about 18 solubilizing moieties, more preferably from about 2 to about 6 solubilizing moieties. These marker components show decreased aggregation in aqueous solution. These marker components show diminished non-specific binding to components of human serum such as human serum albumin ("HSA"). Also these marker components exhibit extended measured fluorescence decay times.

These marker components are advantageously compatible with aqueous solutions, exhibit favorable fluorescence properties including high fluorescence intensity and exhibit decreased non-specific binding to macromolecules in solution.

Accordingly, in general, preferred are fluorophores which efficiently produce fluorescence upon excitation with light whose wavelength falls within the range of about 200 to about 1000 nanometers, preferably in the range of about 600 to 800 nanometers.

Suitable fluorophores include those which absorb and/or emit at wavelengths which are distinguishable from the excitation and emission maxima of the other solution components (such as proteins present in a sample) to minimize background fluorescence.

Since these marker components are particularly useful in assays using samples of biological fluids, for those uses, preferred are fluorophores having excitation and/or emission wavelengths of at least about 500 nanometers which reduces interference from the ambient fluorescence of other sample components. Some samples, such as serum, may exhibit considerable interfering background fluorescence from flavins, flavoproteins, NADH, etc. when excitation wavelengths less than 500 nm are used. Preferred fluorophores may also exhibit a high degree of fluorescence polarization, preferably greater than about 10% of the theoretical maximum value for an observable polarization. For certain applications, such as fluorescence polarization immunoassays, preferred fluorophores are also characterized by measured fluorescence decay times in the range of about 1 nanosecond to about 50 nanoseconds, preferably in the range of about 5 to about 20 nanoseconds. For other applications, such as use as phosphorescent labels, fluorophores having even longer decay times may be used.

Suitable are fluorophore moieties which comprise a luminescent substantially planar molecular structure.

One class of preferred fluorophore moieties comprise a substantially planar multidentate macrocyclic ligand coordinated to a central atom which is preferably in the +3 or +4 oxidation state. Preferred elements for the central atom include silicon, aluminum, germanium, tin, phosphorus and the like; particularly preferred are aluminum, silicon, and germanium. Especially preferred fluorophores comprise multidentate macrocyclic ligands forming a coordination complex with a central atom or ion. Additional coordination sites of this atom or ion may be occupied by at least one solubilizing polyoxyhydrocarbyl moiety. Preferred ions include aluminum (III), silicon (IV), and germanium (IV), which are small ions and there for do not detract from the fluorescence of the macrocyclic ligand, i.e. by spin-orbit coupling. Particularly preferred atoms are those such as silicon which, in the +4 oxidation state, forms an octahedral coordination complex containing two ligands in addition to the macrocyclic ligand. It has been surprisingly found that marker components having two suitably chosen solubilizing groups acting as axial (trans) ligands of a fluorescent octahedral coordination complex exhibit diminished or undetectable non-specific binding to human serum albumin and other solution components.

Thus, preferred are fluorophores which produce fluorescent light efficiently, i.e. which are characterized by high absorbtivity at the appropriate wavelength and high fluorescence quantum yields. For certain applications, preferred fluorophores have measured fluorescence decay times on the order of at least 2 nanoseconds and exhibit a high degree of fluorescence polarization.

Preferred solubilizing polyoxyhydrocarbyl moieties include water soluble carbohydrates such as glucose, sucrose, maltotriose, and the like; water soluble carbohydrate derivatives such as gluconic acid and mannitol and oligosaccharides; polypeptides such as polylysine and naturally-occurring proteins; and water soluble polymers such as polyvinylpyrrolidone, poly(vinylalcohol), poly(ethylenimine), polyacrylic acid, polyacrylamide, ethylene oxide copolymers such as Pluronic ™ (a propylene oxide copolymer, available from BASF) and Tetronic ™ (BASF) polyol surfactants; and polyethers, including water soluble polyoxyalkylene polymers, particularly poly(ethylene glycol) ("PEG") and poly(ethylene glycol) derivatives such as poly(ethylene glycol) methyl ether, amine-terminated poly(ethylene glycol), poly(ethylene glycol) silicon derived esters and the like.

In one aspect of the present invention, at least one solubilizing polyoxyhydrocarbyl moiety is attached to the fluorophore moiety, either to a central atom chelated by the macrocycle or directly to the macrocycle itself. Preferably one to about 18 solubilizing groups are linked to the fluorophore, more preferably from about 2 to about 6 solubilizing groups are attached to the fluorophore moiety.

In another aspect, the present invention is directed to marker components wherein the solubilizing polyoxyhydrocarbyl moiety comprises a ligand which occupies a coordination site of a central atom. Additional coordination sites of this atom are occupied by a fluorescent (multidentate) ligand. For example, where the fluorophore comprises a substantially planar macrocyclic ligand, such as a porphyrin or azaporphyrin derivative whose inner nitrogen atoms occupy coordination sites of the central atom, the solubilizing moiety also acts as a ligand, occupying remaining coordination sites of the central atom. Thus, the solubilizing moiety is orientated so as to be spatially substantially normal to the plane of the macrocycle.

These marker components may be used as labels for labelling an analyte, antigen, antibody or other molecule. These marker components may optionally be functionalized so as to include a linker arm which allows the marker component to be linked to the analyte, antigen, antibody or other molecule. A wide variety of linker arms which are suited to this purpose have been described. (Ref. 17).

Thus, the present invention provides marker components which serve as fluorescent labels and which are useful in fluorescent probes and which have the advantageous properties of diminished non-specific binding to human serum albumin; decreased solvent sensitivity, including high fluorescence intensity and decreased aggregation in aqueous solution; excitation and/or emission wavelength maxima which minimize interference from ambient fluorescence; and fluorescence lifetimes which minimize interference from background fluorescence and scattering.

Definitions

As used herein, the following terms have the following meanings unless expressly stated to the contrary:

The term "analyte" refers to the compound or compound to be measured in an assay which may be any compound for which a receptor naturally exists or can be prepared which is mono- or polyepitopic, antigenic or haptenic, a single or plurality of compounds which share at least one common epitopic site or a receptor.

The term "axial ligand" refers to a substituent which, together with a macrocyclic ligand, forms a coordination complex. The axial ligand lies normal to the plane described by the macrocyclic ligand.

The term "fluorescent probe" refers to a marker component comprising a fluorophore moiety which is bonded to or coordinates either directly or via a linker arm to an analyte, antigen, hapten, antibody or other molecule which is used in an assay, such as a fluoroimmunoassay to determine the presence of and/or quantitate a substance of interest.

The term "solvent sensitivity" refers to changes in the fluorescence behavior of a molecule depending on the solvent system in use, most notably referring to differences in fluorescence behavior in aqueous solution in comparison with organic solvents (such as DMF). Many fluorophores which exhibit high fluorescence intensity in organic solvents such as DMF show substantially decreased fluorescence intensity in aqueous solution.

The quantum yield or quantum efficiency of a compound is the ratio of total quanta emitted per quantum of energy absorbed:

$$\Phi = \frac{\text{number of quanta emitted}}{\text{number of quanta absorbed}}$$

the higher the value of $\Phi$, the greater the fluorescence of the compound.

Fluorescence intensity is related to sample concentration and the intensity of the exciting radiation. The fluorescence intensity of a particular dye can be correlated to its characteristic light absorptivity (extinction coefficient) and fluorescence quantum efficiency, as well as environmental factors.

The term "specific binding pair" refers to two different molecules (or compositions) wherein one of the molecules has an area on the surface or in a cavity which specifically recognizes and binds to a particular spatial and polar organization of the other molecule or molecular complex involving other molecules.

The term "binding partner" refers to a molecule or molecular complex which is capable or specifically recognizing or being recognized by a particular molecule or molecular complex and with that particular molecule or molecular complex forms a specific binding pair.

DETAILED DESCRIPTION OF THE INVENTION

I. PREFERRED MARKER COMPONENTS

Figure 1:
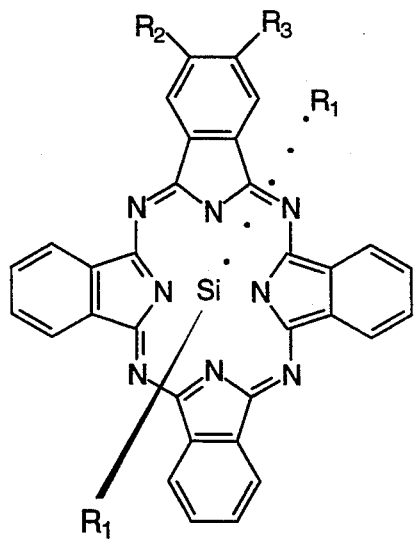
FIG. 1 depicts the structures of compounds I to VIII prepared according to the Examples.
Figure 1:
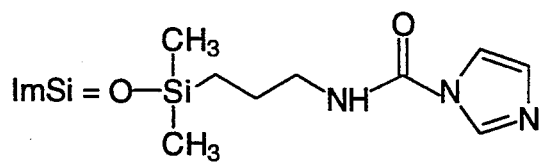
Figure 1:
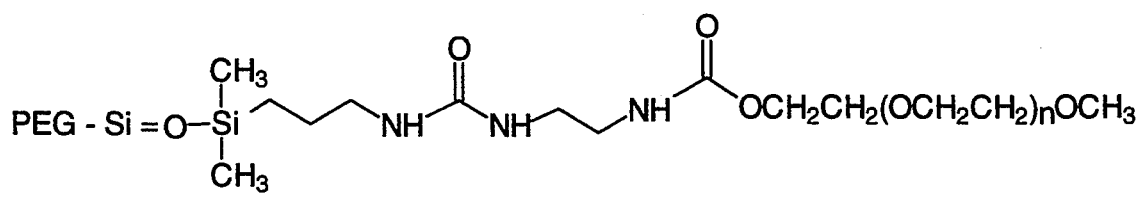

In one aspect, the present invention is directed to marker components wherein the fluorophore moiety comprises a macrocyclic fluorescent dye compound. Preferred are dye compounds having aromatic π-electron systems. Preferably these dye compounds are substantially planar. Optionally, these dye compounds may act as a multidentate ligand to coordinate a central atom. Suitable central atoms include elements capable of forming stable coordination complexes with such multidentate macrocyclic ligands.

In one aspect of the present invention, at least one solubilizing polyoxyhydrocarbyl moiety is linked to the fluorophore moiety directly to the macrocyclic ring. Preferred are marker components from one to about 18 solubilizing moieties, preferably having two or more solubilizing polyoxyhydrocarbyl moieties per fluorophore moiety, especially preferred are those having from about 2 to about 6 solubilizing moieties per fluorophore moiety.

In another aspect, where the macrocycle chelates a central atom, a solubilizing polyoxyhyhydrocarbyl moiety is coordinated to the central atom as an axial ligand. Preferred are marker components having two solubilizing moieties as two axial ligands.

A. Preferred Fluorophore Moieties

Preferred fluorophore moieties include fluorescent dyes having (a) a high extinction coefficient, at least about 1000, preferably greater than 50,000; (b) sufficiently long excitation and emission wavelength maxima so that interference from natural fluorescence of the components in the sample to be assayed is minimized; and (c) high fluorescence intensity. For certain applications, it may be preferred that these fluorophores exhibit (d) a sufficiently long measured fluorescence decay time to allow accurate measurement of emitted light over background fluorescence and scattering (at least about 2, preferably at least about 10 nanoseconds).

Suitable excitation wavelengths range from about 200 nm to about 1000 nm, preferably from about 500 nm to about 900 nm, more preferably from about 650 nm to about 800 nm. These wavelengths are especially preferred in part due to the physical characteristics of the electrical transducers used to generate and detect fluorescence (i,e., laser source and photomultiplier tube).

For certain applications, such as fluorescent polarization immunoassays, it is preferred that the fluorophore has a measured fluorescence decay time in the range of from about 2 nanoseconds to about 50 nanoseconds, more preferred about 10 to about 20 nanoseconds. Fluorescence lifetimes of about 20 nanoseconds are especially preferred.

In another aspect of the present invention, preferred are fluorophores having Stokes shifts of at least about 20 nm, preferably greater than about 50 nm.

As noted, in one aspect of the present invention, preferred fluorophores include macrocyclic fluorescent dye compounds, especially compounds having aromatic π-electron systems. These dye compounds act as multidentate macrocyclic ligands to chelate a central complexing atom. Thus, these preferred fluorophore moieties may comprise a substantially planar multidentate macrocyclic ligand coordinated to a complexing central ion or atom. Preferred elements include aluminum, phosphorous, and the group IVB elements, e.g. silicon, germanium and tin. Such preferred fluorophores include substantially planar multidentate macrocyclic ligands coordinated to a central atom which is able of coordinating with a solubilizing polyoxyhydrocarbyl moiety as an axial ligand. Such preferred elements include aluminum, silicon and germanium. Particularly preferred are elements, such as silicon and germanium, which may form octahedral coordination complexes containing two ligands with a trans (axial) orientation, i.e. on either side of and normal to the planar macrocyclic ligand. It has been surprisingly found that marker components having two solubilizing moieties as axial ligands to the central atom of the fluorophore moiety exhibit especially diminished non-specific binding to biological macromolecules.

Particularly preferred fluorophores include compounds which comprise macrocyclic multidentate nitrogen-containing ligands. In view of the fact that they incorporate most of the above noted preferred characteristics, an especially preferred class of fluorophores comprise porphyrin derivatives and azaporphyrin derivatives with one to four meso-aza bridges (i.e. wherein at least one of the bridging carbon atoms is replaced by a nitrogen atom). Azaporphyrin derivatives include derivatives of mono-, di- and triazaporphyrin and porphyrazine. These macroycycles may optionally include fused aromatic rings, thus, the azaporphyrin derivatives may include, for example, phthalocyanine, benzotriazaporphyrin and naphthalocyanine derivatives. The preparation and fluorescent qualities of these dyes are known (See e.g. Ref. 11, 12, 15) and many of these compounds are commercially available.

Preferred porphyrin and azaporphyrin derivatives include the following and derivatives thereof: hematoporphyrin, deuteroporphyrin, tetra-4-carboxyphenyl-porphyrin, hydoxyaluminum tetracarboxy-phthalocyanine, hydroxyaluminum aminophthalocyanine, hydroxyaluminum tetraaminophthalocyanine, tetrabenzotriazaporphyrin, tetrabenzodiazaporphyrin, tetrabenzomonoazaporphyrin, 1,2-naphthalocyanine, 2,3-naphthalocyanine, tribenzotetraazaporphyrin, chloroaluminum octachlorophthalocyanine, dihydroxysilicon phthalocyanine, dihydroxygermanium phthalocyanine and the like.

For certain applications, such as fluorescence polarization assays, preferred are azaporphyrin derivatives which exhibit a high degree of polarization, that is, those which emit strongly polarized light. For these applications, preferred are macrocycles having lower degrees of symmetry, preferably having lower symmetry than $D_{4h}$. One preferred group includes macrocycles having at least one fused aromatic ring. Thus, preferred macrocycles include azaporphyrin derivatives having fused aromatic rings at positions which result in decreased symmetry and unsymmetrically substituted azaporphyrin derivatives such as 2,3-dicyanophthalocyanine. Preferred classes of azaporphyrin derivatives comprise monoazaporphyrin, diazaporphyrin and triazaporphyrin derivatives, preferably having lower than $D_{4h}$ symmetry.

B. Preferred Solubilizing Polyoxyhydrocarbyl Moieties

Preferred solubilizing polyoxyhydrocarbyl moieties include water soluble carbohydrates such as glucose, sucrose, maltotriose and the like; water soluble carbohydrate derivatives such as gluconic acid and mannitol, and oligosaccharides; polypeptides such as polylysine and naturally occurring proteins; and water soluble polymers such as polyvinylpyrrolidone, poly(vinyl alcohol), poly(ethylenimine), polyacrylic acid, polyacrylamide, ethylene oxide copolymers such as Pluronic TM (a propylene oxide copolymer, available from BASF) and Tetronic TM (BASF) polyol surfactants and, in particular, polyethers such as other polyoxyalkylenes including poly(ethylene glycol), or other water soluble mixed oxyalkylene polymers, and the like.

A particularly preferred class of solubilizing polyoxyhydrocarbyl moieties comprises poly(ethylene glycol) (PEG) and poly(ethylene glycol) derivatives, including poly(ethylene glycol) methyl ethers such as poly(ethylene glycol) monomethyl ether. Other suitable PEG derivatives include PEG-silicon derived ethers, optionally having ureido linkers (See Examples 4 and 6). Many of these polymers are commercially available in a variety of molecular weights; others may be conveniently prepared from commercially available materials, such as by coupling of an amino PEG to a functionalized siloxane moiety (See Example 5). Alternatively an amino-terminated PEG may be coupled to an N-(carboxyimidazo)amino-propyl dimethylsilyl ether linked to the central atom of a macrocyclic ligand.

When linked to a fluorophore moiety, these solubilizing polyoxyhydrocarbyl moieties impart particularly advantageous qualities of solubility in aqueous solution with improved measured fluorescence decay time, and improved fluorescence intensity. Moreover, the resulting marker components are water soluble and show decreased non-specific binding, especially decreased binding to serum albumin which has heretofore been a problem with certain fluorophores, particularly porphyrin or phthalocyanine dyes which have been functionalized with groups such as sulfonate to impart increased water solubility to the molecule. Non-specific binding of fluorophore or marker component impairs the accuracy of the resulting immunoassay. These marker components which comprise fluorophore linked to PEG may also exhibit improved fluorescence intensity in aqueous solution.

Suitable PEGs may vary in molecular weight from about 200 to about 20,000 or more. Choice of a particular molecular weight may depend on the particular fluorophore chosen and its molecular weight and degree of hydrophobicity, as well as the particular application for which the marker component is to be used.

II. PREPARATION OF MARKER COMPONENTS

A. Preparation of Marker Components Having the Solubilizing Polyoxyhydrocarbyl Linked to a Macrocyclic Fluorophore Preparation of marker components having at least one solubilizing polyoxyhydrocarbyl moiety linked to a macrocyclic fluorophore is described in Example 1.

B. Preparation of Marker Components Having Porphyrin and Azaporphyrin Derivatives As Fluorophores and Solubilizing Moieties Attached as Axial Ligands Preparation of porphyrin and azaporphyrin ("Mcl") derivatives which serve as macrocyclic ligands chelating a central atom are described below. The central atom is capable of forming a coordination complex containing both the macrocyclic ligand and at least one additional ligand. Reactions which involve the exchange of groups (or ligands) coordinated to a metal atom are commonly called ligand exchange reactions. In the present context, ligands are defined as groups attached to the central atom of a macrocyclic complex. This central atom may be a metal such as aluminum, or an atom capable of forming bonds having highly covalent character such as silicon. Thus, in ligand exchange reactions, the central atom may be a nonmetal, even carbon. The general scheme for a "ligand exchange reaction" is as follows:

wherein Mcl represents a macrocyclic ligand and CA the central atom.

This ligand-exchange type of reaction has been studied extensively (See, e.g., Ref. 13, 15).

We have found that such reactions advantageously allow incorporation of one or two solubilizing polyoxyhydrocarbyl moieties as axial ligand(s).

III. UTILITY

The marker components of the present invention are useful as fluorescent labels for fluorescent probes for uses such as fluorescence immunoassays. These marker components are also useful as labels for separation assays and as phosphorescent labels in immunoassays. These marker probes are also useful as labels for in vivo imaging and in vivo tumor therapy.

These marker components may be advantageously used as fluorescent labels in conventional fluorescence immunoassays, including fluorescence polarization immunoassays. When so used, these marker components may be linked to one member of a specific binding pair ("labelled binding partner") or an analog of such a member. The marker component may be directly attached or conjugated thereto or attached or conjugated via a linker arm.

These labelled binding partners are useful in assays having a variety of formats, such as assays which involve competition for analyte or analyte binding partner (if a labelled analyte or analyte-analog as used) and may be used in either homogeneous or heterogeneous assays.

In view of their advantageous freedom from aggregation in aqueous solution and lack of solvent sensitivity (indicating no detectable aggregation) in combination with their lack of nonspecific binding to serum components and other biological macromolecules, these markers are especially suited for use in assays for detecting an analyte in a sample containing a biological fluid such as serum. Thus, these marker components may be used as labels for fluorescent probes for detecting analytes in solutions where non-specific binding by serum components would severely compromise sensitivity of an assay, affecting both its accuracy and precision.

Alternatively, these marker components may be used as agents for in vivo imaging. When used as imaging agents, these marker components are conjugated to one member of a specific binding pair to give a labelled binding partner. The labelled binding partner is introduced into an animal. If the other member of the specific binding pair is present, the labelled binding partner will bind thereto and the signal produced by the marker component may be measured and its localization identified.

These marker components may also be used in in vivo tumor therapy. For example, photodynamic therapy involves using the marker component as a photosensitizing agent. The marker component (fluorescent label) is conjugated to a binding partner which may specifically recognize and bind to a component of a tumor cell. The localized fluorescent emission from the bound marker component conjugate after excitation by light, causes selective damage and/or destruction to the tumor cells.

To assist in understanding the present invention, the following examples are included which describe the results of a series of experiments. The following examples relating to this invention should not, of course, be construed in specifically limiting the invention and such variations of the invention, now known or later developed, which would be within the purview of one skilled in the art are considered to fall within the scope of the invention as described herein and as hereinafter claimed.

EXAMPLES

EXAMPLE 1

PREPARATION OF PORPHYRIN DERIVATIVE MARKER COMPONENTS

Deuteroporphyrin IX was purchased from Porphyrin Products (Logan, Utah). Hematoporphyrin, protoporphyrin IX, N,N dimethylformamide (DMF), dicyclohexylcarbidiimide (DCC), 1-hydroxybenzotriazole (HOBT), and 4-dimethylaminopyridine (DMAP) were purchased from Aldrich Chemical Co., Milwaukee, Wis. All chemicals used in the synthesis of phthalocyanine derivatives, including the tetrabenzotriazaporphin derivatives, were purchased from Aldrich. Amine-terminated polyethyleneglycol (PEG-NH$_2$) and phthalocyanine derivatives were synthesized according to published procedures. (Ref. 18).

A. Hematoporphyrin (0.01 mmol) was placed in a flask with HOBT (0.02 mmol), PEG-NH$_2$ (0.02 mmol, MW=2000). DMF (0.4 ml) was added and the resulting solution was stirred at 15° C. while DCC (0.025 mmol) was added in one portion. Stirring was continued for 12 hours at 15° C. At this time, solvent was removed under reduced pressure. The crude product, which was freely soluble in water, was purified by chromatography, e.g. size exclusion chromatography. The yield of hematoporphyrin bispolyethyleneglycol amide was 80–100%.

B. Deuteroporphyrin (0.01 mmol) was placed in a flask with DMF (0.4 ml). The mixture was stirred at 25° C. while carbonyldiimidazole 0.02 mmol was added in one portion. After stirring for two hours at 25° C., mannitol (0.2 mmol) was added and the mixture was stirred at 90° C. for 4 hours. The reaction mixture was allowed to cool to room temperature. Solvent was then removed under reduced pressure and the crude product, which was water-soluble, was purified by chromatography. The yield of deuteroporphyrin esters was 40–80%.

C. Hydroxyaluminum-tetraamino phthalocyanine (0.01 mmol) was placed in a flask along with succinic anhydride (0.08 mmol). Pyridine (0.1 ml), and DMF (0.5 ml) were added and the mixture was heated on a steam bath for 20 minutes. After cooling to room temperature, the reaction mixture was acidified with 50% HCl, diluted with isopropyl alcohol (8 ml), and the precipitated product was collected, washed with isopropyl alcohol, and dried. The yield of hydroxyaluminum-tetrasuccinamidophthalocyanine was 90%. Hydroxyaluminum-tetrasuccinamidophthalocyanine (0.01 mmol), was placed in a flask with polyethyleneglycol monomethyl ether (0.01 mmol, MW=750), DCC (0.1 mmol), DMAP (0.04 mmol), and DMF (1.0 ml). The mixture was stirred at 20° C. for 20 hours. At this time, solvent was removed under reduced pressure, and the water soluble product was purified by chromatography. The yield of the corresponding tetra-ester was 70–90%.

D. A solution containing hematoporphyrin IX (2 mg) and carbonyldiimidazole (2 mg) in dry DMF (2 ml) was stirred at 40° C. for 0.5 hours. At this time polyethylene glycol (M.W. 4000, 200 mg) is added and the solution is heated to 100° C. for an additional 4 hours. The highly water soluble product is hematoporphyrin IX di(polyethylene glycol) ester, which exhibited favorable solution and solution fluorescence properties.

EXAMPLE 2

EFFECT OF NON-SPECIFIC BINDING TO SERUM ALBUMIN ON POLARIZATION

Measurable polarization can be induced either by the binding of the dye to a very large molecule such as serum albumin or by use of a viscous solvent.

The polarization factor was measured for various porphyrin derivatives, in the presence of the noted amount of human serum albumin (HSA) solution, in the absence of HSA (in buffer alone) or in glycerol. Some of the porphyrin derivatives, where noted, were covalently linked to a solubilizing polyoxyhydrocarbyl moiety.

Non-specific binding of porphyrin derivatives to HSA will result in increases in the polarization factor over porphyrin in buffer, aqueous saline azide phosphate ("SAP"), alone. No polarization is expected in SAP.

Each sample was present in solution at a concentration of about $1 \times 10^{-4}$ mole per liter. Excitation was carried out using a laser source which was continuously adjustable from 350 nm to 820 nm (set to about 625 nm), 600 ps to 5 ns pulse width with 3 different nitrogen pump lasers (10–50 micro joule/pulse). The intensity of the fluorescence was measured as a function of time. Polarization of the perpendicular and parallel components was recorded separately. Polarization was expressed as a quotient which may vary from 0 (not polarized) to about 0.2 for these porphyrin derivatives (when completely polarized), since porphyrin derivatives generally exhibit moderate polarization. The polarization quotient of a molecule in solution exhibiting optimal polarization under conditions which are optimal for producing an observable polarization would be 0.5.

Hematoporphyrin IX ("HP") and Protoporphyrin IX ("PP") were obtained from Aldrich. Deuteroporphyrin IX disulfonic acid, sodium salt ("DP-(SO$_3$)$_2$") was obtained from Porphyrin Products (Logan, Utah).

Diesters of porphyrin derivatives with sucrose, mannitol, maltotriose or with a polyethyleneglycol-monomethyl ether ("PEG"*) were prepared according to the methods described in Example 1 herein. The HSA solution used was an aqueous stock solution of 5 weight percent HSA. DMF is N,N-dimethyl-formamide.

Number following PEG specifies approximate molecular weight.

Results are tabulated in Table I.

EXAMPLE 3

PREPARATION OF PHTHALOCYANINE DERIVATIVE MARKER COMPONENTS

Chloroaluminum phthalocyanine (Aldrich Chemical Co.) and dichlorosilicon phthalocyanine (Aldrich Chemical Co.) were hydrolysed to the corresponding hydroxy compounds: hydroxyaluminum phthalocyanine and dihydroxysilicon phthalocyanine, respectively according to conventional methods. (Ref. 12).

A. Preparation of Bis-polyethyleneglycol Silicon Phthalocyanine

In a flask, dihydroxysilicon phthalocyanine (0.02 mmol), polyethylenegylcol monomethyl ether (molecular weight 2000 daltons, 0.02 mmol) and lauric acid (0.02 mmol) were placed. The mixture was stirred and slowly heated to 220° C. The reaction mixture was maintained at that temperature for one hour.

The dark blue reaction mixture was allowed to cool to room temperature, and then was applied directly to a size exclusion chromatography column. The highly water soluble bispolyethylene glycol silicon phthalocyanine was obtained in about 90% yield.

This product showed optimal fluorescence in water or in a biological or physiological buffer. Its fluorescence polarization and fluorescence intensity in a biological phosphate buffer were not affected by the presence of human serum (3% v/v). Non-specific binding to this product to serum components was not detected.

B. Preparation of Polyethyleneglycol Aluminum Phthalocyanine

In a flask, hydroxyaluminum phthalocyanine (0.02 mmole), polyethyleneglycol (molecular weight 2000 daltons, 0.4 mmol) and lauric acid (0.02 mmol) were placed. The mixture was heated to about 250°–280° C. for one hour. After cooling, the reaction mixture was applied to a chromatography column. The yield of polyethyleneglycol aluminum phthalocyanine was approximately 70%.

This product, although highly water soluble, showed some aggregation as evidenced by its visible light absorption and fluorescence spectra. The fluorescence intensity of this material (concentration $1 \times 10^{-6}$ M, excitation wavelength 690 nm) in water or a biological buffer increased to greater than 150% of its original value upon addition of human serum (3% v/v). Furthermore, an observable polarization of fluorescence was produced upon addition of human serum to the sample. These results indicated that this product did exhibit some non-specific binding to macromolecules present in human serum.

EXAMPLE 4

PREPARATION OF A WATER-SOLUBLE BIS-POLYETHYLENEGLYCOL SILICON PHTHALOCYANINE

Chloropropyldimethylchlorosilane was purchased from Petrarch Systems.

Dihydroxysilicon phthalocyanine (0.16 mmol), imidazole (0.7 mmol), and dry DMF (1 ml) were placed in a flask and stirred at 20° C. while chloropropyldimethylchlorosilane (0.7 mmol) was added dropwise, taking care to exclude atmospheric moisture. Stirring at 20° C. was continued for 20 hours.

At this time, solvent was removed under reduced pressure, and the product applied to a silica gel chromatography column. Elution with CH$_2$Cl$_2$-hexane (1:1) afforded a single major colored fraction, SiPc-[OSi(CH$_3$)$_2$CH$_2$CH$_2$CH$_2$Cl]$_2$ (compound I).

The NMR spectrum of compound I was recorded on a General Electric QE-300 Spectrometer. NMR (CDCl$_3$): δ 9.65 (m, aromatic, 4H), δ 8.45 (m, aromatic, 4H), δ 2.1 (t, CH$_2$-Cl, 2H), δ −0.85 (m, CH$_2$, 2H), δ −2.09 (m, CH$_2$-Si, 2H), δ −2.85 (s, CH$_3$, 6H).

A. Compound I (0.01 mmol) was placed in a flask with amine-terminated polyethyleneglycol, MW 2000 (0.2 mmol), sodium iodide (0.01 mmol) and DMF (1 ml), and the mixture was heated and stirred at 90° C. for 15 hours.

Removal of solvent under reduced pressure afforded a viscous blue liquid which was purified by chromatography. This product, SiPc[OSi(CH$_3$)$_2$CH$_2$CH$_2$CH$_2$NH-PEG]$_2$, was highly water soluble and exhibited strong fluorescence in aqueous solution. The fluorescence of this material as a solution in a biological buffer was not affected by the addition of human serum albumin (3 volume %).

B. Compound I (0.01 mmol) is placed in a flask with amine-terminated polyethyleneglycol, MW 600 (0.2 mmol), sodium iodide (0.01 mmol) and DMF (1 ml), and the mixture is heated and stirred at 90° C. for about 15 hours.

Removal of solvent under reduced pressure affords a viscous blue liquid which is purified by chromatography.

EXAMPLE 5

PREPARATION OF A WATER SOLUBLE BIS-POLYETHYLENE GLYCOL SILICON PHTHALOCYANINE

A. Preparation of Phthalocyaninato-bis-[3-(1H-imidazol-1-ylcarbonyl-)aminopropyldimethylsilanolato]silicon (compound II)

In a flask was placed dihydroxysilicon phthalocyanine (100 mg), imidazole (150 mg), and DMF (2.0 ml). The contents of the flask were stirred while isocyanatopropyldimethylchlorosilane (0.150 ml) was added over a period of one minute. The flask was sealed to exclude moisture and the reaction mixture was stirred at room temperature for 30 hours.

The flask was opened and its contents were diluted to 5 ml with methanol. Removal of solvent on a rotary evaporator under high vacuum left a residue which was transferred to a silica gel chromatography column prepared using toluene and 230–400 mesh silica gel (EM Science). Elution with toluene: isopropanol (85:15) afforded the separation of a deep blue fraction which was collected. Removal of solvent left a crystalline solid. Proton NMR (CDCl3): δ −2.84 (s, 12H), δ −2.10(t, 4H), δ −1.10 (m, 4H), δ1.9 (m, 4H), δ 7.23 (m, 4H), δ 8.02 (s, 2H), δ 8.30 (m, 8H), δ 9.62 (m, 8H).

B. Reaction of Compound II with Amine-Terminated PEG (Compound III)

The reactive intermediate from step A above (10 mg) was placed in a flask along with amine-terminated polyethyleneglycol (MW-2000, 50 mg) and methanol (3 ml) and the mixture was refluxed for one hour. Removal of solvent left a blue oil which was purified by HPLC using a C18 stationary phase and 80% methanol as eluant. The yield of this material was 40–70% based on the starting dihydroxysilicon phthalocyanine. The purified material exhibits intense fluorescence in aqueous solution as well as in organic solvents such as methanol and dimethylformamide (excitation of fluorescence at 675 nm). This compound has been assigned the structure shown for compound III in FIG. 1.

EXAMPLE 6

PREPARATION OF A PHTHALOCYANINE DERIVATIVE WHICH IS USEFUL AS A PROBE IN A FLUORESCENCE POLARIZATION IMMUNOASSAY

A. Preparation of Diiminoisoindoline

In a three-neck, 100 ml round-bottom flask fitted with a reflux condenser and a gas inlet tube was placed phthalonitrile (12.8 g), and methanol (50 ml), and the mixture was stirred while ammonia gas was slowly introduced. In order to prevent the possible flow of the reaction mixture into the ammonia source, and in-line trap was employed. After the reaction mixture appeared to be saturated with ammonia, 0.33 g of dry potassium tert-butoxide was added with stirring.

Stirring was continued and the reaction mixture was heated to reflux for three hours with continued introduction of ammonia. Care was taken to avoid fouling of the gas inlet with the crystalline product. At the end of the reflux period a pale green solid had formed. The solid was collected by filtration and washed with a small volume of cold (4° C.) methanol. (This compound is appreciably soluble in methanol). This material was dried and used for the next step without further purification. Yield was 7 g (about 50%).

B. Preparation of Dicyanodiiminisoindoline 1,2,4,5-Tetracyanobenzene (Pfaltz & Bauer, 0.5 g, 2.8 mmol) was suspended in methanol (10 ml) in a three-neck round-bottom flask fitted with a reflux condenser and a gas inlet tube. The mixture was stirred at 25° C. without external cooling while ammonia gas was rapidly introduced. During the first two minutes of ammonia introduction the temperature of the reaction mixture rose to greater than 50° C. and the suspended solid dissolved completely. Within 5 minutes a precipitate began to form. Stirring at 40°–50° C. with slow introduction of ammonia was continued for 1 hour. The precipitated solid was collected by filtration, washed with methanol, and dried. This product exhibits a very low solubility in methanol.

C. Preparation of Dicyanosiliconphthalocyanine Dichloride (Compound V)

In a dry 50 ml round-bottom flask was placed dicyanodiiminoisoindoline (350 mg, 1.8 mmol) along with diiminoisoindoline (1.0 g, 6.9 mmol) and quinoline (Fluka, 20 ml). The mixture was stirred at 25° C. while silicon tetrachloride (Aldrich, 2.0 ml, 18 mmol) was added dropwise over a period of 1 minute. The flask was then fitted with a reflux condenser (using teflon tape) and a calcium chloride drying tube and stirred for one minute at 25° C.

At this time the reaction flask was lowered into a large oil bath maintained at 180°–185° C. and efficient magnetic stirring was continued for 30 minutes. The oil bath was then removed and the contents of the flask were allowed to cool to room temperature.

The dark reaction mixture was carefully treated with water (5 ml) and then diluted with 45 ml of a 30% HCl solution. The resulting dark precipitate was collected by filtration on a 10 cm Buchner funnel. Washing with water and then acetone left a blue solid (1 gram) which was air dried and used without further purification for the next reaction step.

D. Hydrolysis of Dicyanosiliconphthalocyanine Dichloride (Compound VI)

The crude dicyanophthalocyanine from step (c) (1 gram) was placed in a flask with a stir bar and 6 ml of concentrated sulfuric acid and stirred at 50° C. overnight. The mixture was then carefully diluted with 4 ml water and heated to 100°–100° C. for an additional 20 hours. Cooling and dilution with water (20 ml) gave a blue precipitate which was collected by filtration and washed with water. The solid was then transferred to a flask along with a stir bar and 20 ml of a 1.0 M potassium carbonate solution and stirred and heated at reflux for one hour. The suspension was then slowly and carefully acidified with concentrated HCl and then filtered and the resulting solid was washed with water and acetone and dried in a desiccator. This material (0.7 grams) was used without further purification in the next step.

E. Preparation of 2,3-Dicarboxyphthalocyaninatobis-[3-(1H-imidazol-1-ylcarbonyl)aminopropyldimethylsilanolato]silicon (Compound VII)

The crude silicon phthalocyanine dihydroxide from step (D) (85 mg) was placed in a vial along with a stir bar and imidazole (160 mg, 2.3 mmol) and 1 ml of dry DMF. The mixture was stirred for 5 minutes at 25° C. and then 3-isocyanatopropyldimethylchlorosilane (Petrarch, 110 μl, 0.68 mmol) was added to the stirred mixture over a period of 0.5 minutes. The vial was capped in order to exclude moisture and stirring at 25° C. was continued for 20–40 hours. (A 40 hour reaction time appeared to result in an improved yield). The vial was then opened and the dark blue mixture was diluted with methanol (4 ml) and filtered through #545 celite to remove solids. The filtrate was concentrated on a rotovap using high vacuum and a water bath maintained at 40° C. The dark residue was then slurried with silica gel (1–3 g) and methanol (5 ml) and the methanol was removed on a rotovap under aspirator pressure. The blue residue was then suspended in toluene and transferred to a silica gel column prepared from 15 ml 23–400 mesh silica gel (EM Science) and toluene. This column had been washed with 50% methanol in toluene.

Increasing the solvent polarity by increasing the methanol content of the solvent to 16% brought about the migration of a distinct band which was collected.

This material was saved but not used for further transformations.

Increasing the solvent polarity by slowly increasing the methanol content of the eluant to 30% brought about the migration of a second blue band which was collected within a 20 ml volume of 30% methanol. This material was transferred to a round bottom flask. Removal of solvent on a rotovap under high vacuum at 25° C. left a residue which appeared to include an appreciable quantity of imidazole along with the blue dye. This material was used without further purification for the next step. The yield of compound VII was approximately 3 mg.

F. Preparation of Amine-Terminated Polyethylene Glycol

Poly(ethylene glycol) monomethyl ether (Aldrich, average M.W. 2000, 10 g, 5 mmol) was placed in a 100 ml roundbottom flask along with a stir bar and 55 ml toluene. The flask was fitted with a short-path distillation apparatus and immersed in a heating bath. Toluene was slowly distilled at 760 mm Hg until the distillate was no longer cloudy. This required the removal of about 15 ml of toluene.

The relatively water-free PEG solution was allowed to cool to 40° C. When this temperature had been attained, carbonyldiimidazole (Aldrich, 1.2 g, 7.5 mmol) was added to the stirred solution in one portion. Stirring at 30°–40° C. was continued overnight with protection from atmospheric moisture.

Water (100 μl, 3.75 mmol) was then added to the reaction mixture and efficient magnetic stirring was continued until the evolution of $CO_2$ gas could no longer be observed (about 15 minutes).

Most of the toluene was removed on the rotovap at 30° C. under high vacuum leaving a viscous, colorless oil. This material was diluted with isopropanol (20 ml) and added to a stirred solution of 1,2 ethylenediamine (Fluka, 6.7 ml, 100 mmol) in isopropanol (15 ml) over a period of five minutes. After completion of the addition the clear solution was maintained at 40° C. for four hours.

At this time isopropanol (150 ml) was added to the reaction mixture. The diluted solution was allowed to stand at 4° C. overnight, resulting in the formation of a voluminous mass of white crystals. This solid was collected on a 10 cm Buchner funnel, and subsequently recrystallized from isopropanol.

Drying under high vacuum over sulfuric acid afforded 7 grams of the crude amine, suitable for use as a reagent. Structure of the product was confirmed by IR.

The amine content of polyethyleneglycol amine, prepared as outlined above, was determined to be >70 mole % by the following method:

25 ml of 10% solution of the amine in methanol was allowed to react with an equal volume of a 6% solution of maleic anhydride in THF. The reaction mixture was allowed to stand for 0.5 hours at 25° C. and was then diluted to 1.0 ml with methanol. A 5 μl aliquot of this final solution was injected on to an analytical RP18 reverse phase HPLC column using 30% methanol in water as the initial mobile phase. Using n-propylamine as an internal standard allowed for accurate-quantification of the UV-absorbing acyl-PEG derivative, which was eluted in 80% methanol and was detected at 254 nm.

Analysis of the infrared spectrum of amine-terminated PEG can also provides a convenient means of estimating the product yield.

G. Reaction of Compound VII with Amine-Terminated Polyethylene GlyCol (Compound VIII).

The product of step (E) (Compound VII) (3 mg, $5 \times 10^{-3}$ mmol), which had been obtained in partially purified form by chromatography on silica gel, was dissolved in methanol (1 ml). The mixture was stirred while amine-terminated PEG (product of step (F), 100 mg, $5 \times 10^{-2}$ mmol) was added. The resulting deep blue solution was heated to reflux for one hour.

Removal of methanol under aspirator pressure at 25° C. left a viscous blue oil which was taken up in water (0.5 ml) and applied to a small (10 ml wet volume) DEAE Sephadex anion ion exchange column (Pharmacia, 3.5 meq/g, 40-120 micron, basic form <1M $K_2CO_3$). The water-soluble blue dye was retained quantitatively by the column. The column was washed with water (15 ml) and the blue dye was then eluted in greater than 70% yield with 10–20 ml of a 15% aqueous acetic acid solution.

Water and acetic acid were removed under high vacuum and the blue residue was taken up in a small volume of methanol and applied to a C18 reverse phase semi-preparative HPLC column. The major product, detected at 675 nm as a single peak, eluted with 80% aqueous methanol (containing 0.6% acetic acid) and comprised about 50% of the sum of the material which was recovered from the column. Fractions containing the major product were combined and solvent was removed under high vacuum leaving a blue residue. (approx. 0.5 mg, $10^{-7}$ mmol).

NMR ($DCCl_3$: $\delta$ −2.85 (S, 12H), $\delta$ −2.29 (m, 4H), $\delta$ −1.30 (m, 4H), $\delta$ 1.80 (m, 4H), $\delta$3.6 (br.s, 300–400H), $\delta$ 8.39 (m, 6H), $\delta$ 9.68 (m, 6H), $\delta$ 10.56 (S, 2H). Note: Because the sample had been prevsiouly dissolved in $D_2O$, the acidic protons, RCOOH, were not observed.

EXAMPLE 7

CONJUGATION OF AMINODIGOXIGENIN WITH COMPOUND VIII-A DIGOXIGENIN PROBE

The product of Example 6 (Compound VIII) was placed in a small flask along with 3 α,β-aminodigoxigenin (0.5 mg, $1.3 \times 10^{-6}$ mol), 1-hydroxybenzotriazole hydrate (Aldrich, 0.5 mg, $5.7 \times 10^{-6}$ mol), and 1-(3-dimethylaminopropyl)-3-ethylcarbodiimide hydrochloride (1 mg, $5 \times 10^{-6}$ mol). DMF, (Aldrich, HPLC grade, stored over 4A molecular sieves, 100 μl) was added to the reaction flask and the contents of the flask were thoroughly mixed at 25° C. and then allowed to stand at 4° C. overnight. Most of the solvent was then evaporated under a stream of nitrogen and the residue was taken up in water and applied to an analytical RP18 HPLC column for purification. Detection at 675 nm revealed a single major product (i.e., a single major peak) which comprised more than 70% of the product mixture.

Fractions containing this material were combined, brought to pH 7 with a phosphate buffer, and stored as a stock solution in this medium.

This product gave an immunospecific reaction with a specific digoxin antibody.

TABLE I

POLARIZATION FRACTION OF CERTAIN PORPHYRIN DERIVATIVES

| Porphyrin Derivative | Solvent (Buffer) | μ 1HSA Soln. | Polarization Faction | Fluorescence Lifetime (nsec) |
|---|---|---|---|---|
| HP | SAP | 0 | 0 | — |
| HP | SAP | 2 | 0.2 | — |
| HP-(mannitol)$_2$ | SAP | 2 | <0.01 | — |
| HP-(mannitol)$_2$ | SAP | 22 | 0.07 | — |
| HP-(mannitol)$_2$ | SAP | 50 | 0.14 | — |
| HP-(mannitol)$_2$ | SAP | 100 | 0.2 | — |
| HP-(sucrose)$_2$ | SAP | 0 | 0 | — |
| HP-(sucrose)$_2$ | SAP | 100 | 0.1 | — |
| HP-(PEG 750)$_2$ | SAP | 0 | 0 | — |
| HP-(PEG 750)$_2$ | SAP | 50 | <0.01 | — |
| HP-(PEG 750)$_2$ | SAP | 100 | 0.016 | — |
| HP-(PEG 4000)$_2$ | SAP | 0 | 0 | — |
| HP-(PEG 4000)$_2$ | SAP | 100 | 0 | — |
| HP-(PEG 4000)$_2$ | glycerol | 0 | 0.25 | — |
| DP-(SO$_3$)$_2$ | SAP | 0 | 0 | 12.2 |
| DP-(SO$_3$)$_2$ | SAP | 50 | 0.2 | — |
| PP-(maltotriose)$_2$ | DMF | 0 | 0 | 14 |
| PP-(maltotriose)$_2$ | SAP | 0 | 0 | 10.3 |
| PP-(maltotriose)$_2$ | SAP | 50 | 0.1 | — |
| PP-(PEG 2000)$_2$ | DMF | 0 | 0 | 15.6 |
| PP-(PEG 2000)$_2$ | SAP | 0 | 0 | 17.8 |

BIBLIOGRAPHY

1. T. Ngo (editor); Nonisotopic Immunoassay; Plenum Press, New York pp. 187–210 (1988).
2. L. Kaplan et al. (editors); Nonisotopic Alternatives to Radioimmunoassay; Marcel Dekker, Inc., New York pp. 143–170 (1981).
3. Dandliker et al.; "Fluorescence Polarization Immunoassay. Theory and Experimental Method"; Immunochemistry 10:219–227 (1973).
4. E. Jones et al. (editors); Aggregation Processes in Solution; Elsevier Scientific, New York pp. 241–308 (1983).
5. E. Soini et al.; Fluoroimmunoassay: Present Status; Clinical Chemistry 25: 353–61 (1979).
6. Kirk-Othmer Encyclopedia of Chemical Technology; third edition, John Wiley & Sons, New York Volume 22, pp. 1–45 ("Sulfonation").
7. D. Taylor (editor); Applications of Fluorescence in the Biomedical Sciences; Liss, Inc., New York pp. 3–28 (1985).
8. D. Dorion (editor); Porphyrin Localization and Treatment of Tumors; Liss, Inc., New York (1983).
9. W. Chan et al.; Cell Uptake, Distribution and Response to Aluminum Chloro Sulphonated Phthalocyanine, a Potential Anti-Tumor Photosensitizer.; British Journal of Cancer 53: 255–263 (1986).
10. I. McCubbin; Photochemistry of Some Water-Soluble Phthalocyanines; Ph.D. Thesis, University of London (1985).
11. F. Moser; Phthalocyanine Compounds; Reinhold Publishing Co., New York (1963).
12. G. Wilkinson (editor); Comprehensive Coordination Chemistry; Pergamon Press, New York, Volume 2, pages 813–898 (1987).
13. H. Emeleus et al. (editors); Advances in Inorganic and Radiochemistry; Academic Press, New York, Volume 7, pges 41–49 (1965).
14. D. Guttman et al.; "The Binding of Drugs by Plasma Proteins"; Journal of Pharmaceutical Sciences 57:903 (1968).
15. M. Hanack, et al.; "Synthesis and Properties of a New Kind of One-Dimensional Conductor", Journal of Organometallic Chemistry 204:315–325 (1981).
16. G. Melson (editor); Coordination Chemistry of Macrocyclic Compounds; Plenum Press, New York, pages 474–477 (1979).
17. Kricka, L. J., Ligand-Binder Assays: Labels and Analytical Stratagies, pp. 15–51, (Marcel Dekker, Inc., New York, 1985).
18. Harris, J. M., "Laboratory Synthesis of Polyethylene Glycol Derivatives," in J. Macromol. Sci.-Rev.-Macromol. Chem. Phys., C 25(3):325–373 (1985).

I claim:

1. A detectably labelled marker component which comprises a fluorophore moiety which is linked to one or more solubilizing polyoxyhydrocarbyl moieties wherein said solubilizing polyhydrocarbyl moieties are selected from a polyether, a polyol, or a water soluble polymer and wherein said fluorophore moiety is a porphyrin derivative or an azaporphyrin derivative wherein one or more bridging carbon atoms has been replaced by nitrogen.

2. A marker component according to claim 1 having two or more solubilizing moieties.

3. A marker component according to claim 2 having about 2 to about 6 solubilizing moieties per fluorophore moiety.

4. A marker component according to claim 3 wherein the fluorophore moiety is luminescent.

5. A marker component according to claim 4 wherein the fluorophore moiety has a luminescent substantially planar molecular structure.

6. A marker component according to claim 5 wherein said fluorophore moiety is a nitrogen-containing macrocycle.

7. A marker component according to claim 6 wherein the solubilizing moieties are polyethyleneglycol or a polyethyleneglycol derivative.

8. A marker component according to claim 7 wherein said solubilizing moieties have a molecular weight of from 200 to 20,000.

9. A marker component according to claim 7 wherein said macrocycle is coordinated to a central atom.

10. A marker component according to claim 9 wherein the central atom coordinates a solubilizing moiety as an axial ligand.

11. A marker component according to claim 10 wherein said macrocycle is a porphyrin derivative wherein from 1 to 4 of the bridging carbon atoms is replaced by nitrogen.

12. A marker component according to claim 11 wherein said macrocycle is a phthalocyanine derivative.

13. A marker component according to claim 12 wherein said central atom comprises silicon.

14. A marker component according to claim 9 wherein said macrocycle has a low degree of symmetry so as to enhance the polarization of emission parallel to polarization of absorption.

15. A marker component according to claim 11 wherein said macrocycle has a lower symmetry than $D_{4h}$.

16. A marker component according to claim 15 wherein said macrocycle is a porphyrin derivative wherein 1 to 4 of the bridging carbons is replaced by nitrogen.

17. A marker component according to claim 16 wherein said macrocycle has at least one fused aromatic ring.

18. A marker component according to claim 16 wherein said macrocycle is a derivative of monoazaporphyrin, diazaporphyrin or triazaporphyrin.

19. A marker component according to claim 18 wherein said macrocycle has at least one fused aromatic ring.

20. A marker component according to claim 15 wherein said macrocycle is a porphyin derivative having at least one fused aromatic ring and wherein optionally 1 to 4 of the bridging carbons is replaced by nitrogen.

21. A marker component which is compound VIII of Example 6 and FIG. 1.

22. A detectably labelled marker component of claim 1 which comprises a fluorophore moiety which is linked to at least one solubilizing polyoxyhydrocarbyl moiety wherein said solubilizing moiety is a polyethyleneglycol or polyethyleneglycol derivative of molecular weight of from 200 to 20,000 and wherein said fluorophore moiety is a macrocycle which is a porphyrin derivative or azaporphyrin derivative wherein one or more bridging carbon atoms has been replaced by nitrogen.

* * * * *

UNITED STATES PATENT AND TRADEMARK OFFICE
CERTIFICATE OF CORRECTION

PATENT NO. : 5,403,928
DATED : Apr. 4, 1995
INVENTOR(S) : Peter O. G. Arrhenuis

It is certified that error appears in the above-identified patent and that said Letters Patent is hereby corrected as shown below:

Column 18, Line 6: Delete "GlyCol" and insert --Glycol--

Column 20, Line 17, Claim 1: Delete "polyhydrocarbyl" and insert --polyoxyhydrocarbyl--

Column 21, Line 9, Claim 20: Delete "porphyin" and insert --porphyrin--

Signed and Sealed this

Twenty-ninth Day of May, 2001

*Attest:*

NICHOLAS P. GODICI

*Attesting Officer*      *Acting Director of the United States Patent and Trademark Office*